United States Patent
Lucas et al.

(10) Patent No.: US 6,909,505 B2
(45) Date of Patent: Jun. 21, 2005

(54) METHOD AND APPARATUS FOR MOLTEN MATERIAL ANALYSIS BY LASER INDUCED BREAKDOWN SPECTROSCOPY

(75) Inventors: John M. Lucas, Outremont (CA); Mohamad Sabsabi, Boucherville (CA); René Héon, Boucherville (CA)

(73) Assignees: National Research Council of Canada, Ottawa (CA); Noranda Inc., Pointe-Claire (CA)

( * ) Notice: Subject to any disclaimer, the term of this patent is extended or adjusted under 35 U.S.C. 154(b) by 376 days.

(21) Appl. No.: 10/176,586

(22) Filed: Jun. 24, 2002

(65) Prior Publication Data

US 2003/0234928 A1 Dec. 25, 2003

(51) Int. Cl.[7] ............................. G01J 3/30; G01J 3/42
(52) U.S. Cl. .................... 356/318; 356/317; 356/319; 250/339.01
(58) Field of Search .................. 356/317, 318, 356/319, 326; 250/339.01, 432 R, 573; 73/61.41

(56) References Cited

U.S. PATENT DOCUMENTS

| | | | |
|---|---|---|---|
| 4,925,307 A | | 5/1990 | Cremers et al. |
| 4,986,658 A | | 1/1991 | Kim |
| 4,995,723 A | | 2/1991 | Carlhoff et al. |
| 5,042,947 A | * | 8/1991 | Potzschke et al. .......... 356/318 |
| 5,751,416 A | | 5/1998 | Singh et al. |
| 6,008,896 A | * | 12/1999 | Sabsabi et al. ............. 356/318 |
| 6,008,897 A | | 12/1999 | Sabsabi et al. |
| 6,661,511 B2 | * | 12/2003 | Detalle et al. ............. 356/318 |
| 6,700,660 B2 | * | 3/2004 | Sabsabi et al. ............. 356/318 |
| 2003/0197125 A1 | * | 10/2003 | De Saro et al. ........ 250/339.07 |

FOREIGN PATENT DOCUMENTS

| | | |
|---|---|---|
| GB | 2154315 A | 9/1985 |
| JP | 60042644 | 3/1985 |
| JP | 62254042 | 11/1987 |
| JP | 02254345 | 10/1990 |
| JP | 07234211 | 9/1995 |
| JP | 08219993 | 8/1996 |

OTHER PUBLICATIONS

St–Onge et al, Spectrochimica Acta B, vol. 57, pp. 121–135, 2002.

* cited by examiner

*Primary Examiner*—Layla Lauchman
(74) *Attorney, Agent, or Firm*—L. Anne Kinsman; Borden Ladner Gervais LLP

(57) ABSTRACT

An apparatus and a method are disclosed for use with Laser Induced Breakdown Spectroscopy (LIBS) systems that can be applied to the real time analysis of molten materials or liquid. Since it is difficult to prepare a surface representative of the bulk when dealing with high temperature molten material, the invention, in one aspect, uses a forced gas flow through a tube insertable inside the molten material to generate a bubble. The inner surface of the bubble is a representative of the composition of the material. LIBS performed on such a surface produces an accurate real time analysis of material, even when other processing of material, e.g., copper smelting, etc., is being conducted.

39 Claims, 9 Drawing Sheets

METHOD AND APPARATUS FOR MOLTEN MATERIAL ANALYSIS BY LASER INDUCED BREAKDOWN SPECTROSCOPY

FIELD OF THE INVENTION

This invention relates to an apparatus and method for use in laser induced breakdown spectroscopy (LIBS), and for the rapid analysis of liquids, especially high temperature molten materials such as metals, metallurgical mattes, salts and glasses. In particular, the invention is directed to an apparatus and method for use with LIBS systems that can be applied to the real time analysis of molten materials. The invention may also be applicable to liquids where more than a single phase is present, and where simultaneous analysis of one or more phases is sought.

BACKGROUND OF THE INVENTION

The metal-producing industry continually faces the major challenge of increasing productivity, reducing costs, and maximizing benefits from existing equipment. Production of metals involves the basic steps of melting, processing and refining charges. During processing and refining, it is often critical that operating parameters are adjusted and controlled so the chemistry of the melt is within predetermined limits. Presently, charge compositions in many industrial processes are monitored by periodic sampling followed by time-consuming sample preparation and laboratory analysis. Virtually eliminating this delay through real time in-situ LIBS analysis has the potential to significantly increase productivity and improve process control. Other processes which, for example, involve the control and maintenance of alloys or non-metallic molten baths, such as used in the production of aluminum and magnesium, may also benefit from continuous monitoring of their elemental constituents.

LIBS can provide rapid, in-situ compositional analysis of a variety of materials in hostile environments, and at a distance. This technique involves focusing a high power pulsed laser on a material, thereby vaporizing and ionizing a small volume of the material to produce a plasma or spark having an elemental composition representative of the material. The optical emission of the plasma is analyzed with an optical spectrometer to obtain its atomic composition. Plasmas and sparks are used interchangeably in this specification.

A method for analyzing elements present in a sample using LIBS is known in the art. For example, a list of patents that are related to the technique can be found in U.S. Pat. 5,751,416, issued May 12, 1998 to Singh et al. Furthermore this method has been applied to a variety of materials and industrial environments. Unlike dealing with other liquids, LIBS analysis of high temperature molten materials in processing vessels often presents difficulties due to floating contamination or surface oxidation when the material is exposed to reactive atmospheres. To use the LIBS technique for analyzing molten materials and to overcome these problems, a method of data analysis is combined with means for exposing relatively unadulterated molten material surfaces for LIBS analysis. In the past, to address these problems and carry out LIBS measurements on molten material three approaches have previously been used, as exemplified in the following documents.

British Patent No. 2,154,315A, published Sep. 4, 1985 to Spenceley et al, describes a probe, which can be projected into the vessel to penetrate the surface of the molten metal below the slag layer. The probe is protected at its end by means of a ceramic collar suitably cooled and pressurized, to prevent damage by entry of metal, by a flow of inert gas entering the probe and exiting at a restricted port perpendicular to the probe, and parallel to the surface of molten metal. This approach can be applied only to a stationary stable surface. Further, in this configuration the laser irradiation samples an exposed surface which is not fresh and which is not necessarily representative of the molten metal. Furthermore, the laser irradiation is transmitted through a waveguide (optical fiber), which reduces the depth of field and restricts operation to short distances from the furnace.

U.S. Pat. No. 4,986,658, issued Jan. 22, 1991 to Kim, describes a probe for performing molten metal analysis by laser induced breakdown spectroscopy. The probe contains a high-power laser that produces a pulse with a triangular pulse waveform. When the probe head is immersed in molten metal, the pulsed laser beam vaporizes a portion of the molten metal to produce plasma having an elemental composition representative of the molten metal composition. The probe comprises a pair of spectrographs, each having a diffraction grating coupled to a gated intensified photodiode array. The spectroscopic atomic emission of the plasma is detected and analyzed for two separate time windows during the life of the plasma by using the two spectrometers in parallel. The spectra obtained during either the first or the second time window, or a combination of both, can be used to infer the atomic composition of the molten metal. In this configuration for obtaining an elemental composition representative of the liquid, the probe head must be immersed in the liquid or the molten metal. However, the immersed probe system is not easy to use and is not suitable for use with most molten metals or melt glass. Furthermore the probe samples a stationary surface which is not fresh and is problematic as explained above.

U.S. Pat. No. 4,995,723, issued Feb. 26, 1991 to Carlhoff et al, discloses a method and apparatus for optically coupling an element analysis system based on LIBS to the liquid metal in a melting vessel. A direct access to the slag-free metal bath is achieved through a bore hole in the sidewall of the vessel below the bath level or in the vessel bottom. To prevent liquid from escaping, a gas is blown in so as to produce the necessary counter-pressure. Again in this approach, the surface of the molten metal exposed to the laser irradiation is stationary. Furthermore it is difficult to prevent freezing of the surface.

Two temporally close sparks induced by two collinear lasers are used in U.S. Pat. No. 4,925,307, issued May 15, 1990 to Cremers et al, for the spectrochemical analysis of liquids. The laser light is not significantly absorbed by the sample so that the sparks occur in the volume inside the liquid. The spark produced by the first laser pulse produces a bubble in the liquid that remains in the gaseous state for hundreds of microseconds after the first spark has decayed. The second laser pulse, fired typically 18 microseconds after the first pulse, then produces a second spark within the gaseous bubble. The emission spectrum of the second spark, detected by a spectrometer oriented at 90 degrees to the laser beam axis, is thus much more intense and exhibits reduced line widths compared to the first spark, so that increased detectability of the atomic species is obtained by sampling the bubble with the second laser spark. This approach cannot be used for molten metals, opaque liquids or for real time measurement, as it is only suitable for off-line analysis of relatively transparent liquids.

SUMMARY OF THE INVENTION

Briefly, the technique of the present invention is to continuously monitor various elements in molten material, during processing, to thereby eliminate or reduce the need for removing samples from the melt for laboratory analysis. Direct monitoring of the molten material provides many advantages over discrete sampling, including the ability to adjust the process being monitored in real time according to the results of the analysis. Furthermore, the present invention relates to a method and apparatus for coupling an element analysis system based on laser-induced breakdown spectroscopy to the molten material.

In one aspect, the invention addresses the problem of preparing a portion of the molten material which is representative of its composition so that LIBS performed on it generates an accurate analysis.

In a further aspect of the invention, the direct access to the molten material is achieved through a probe introduced into the molten material while blowing an appropriate gas through the probe tube forming bubbles inside the material at the end of the tube. These bubbles enable the formation of fresh surface of molten material to be exposed to the laser irradiation. The laser beam focused on the surface portion of the melt inside the bubble produces a plasma, which emits radiation specific to the elements present in the plasma. The radiation is directed through the tube and waveguide into a spectrometer for spectral discrimination.

In yet a further aspect, the invention makes use of a vision system which monitors the inner surface of the bubble to assist targeting the laser beam.

In another aspect of the invention, the LIBS probe can be introduced in a molten metal at a different angle so that the bubble can be controlled for a variety of analyzing environments.

In another aspect of the invention, the LIBS probe can be introduced through submerged tuyeres used in certain pyrometalurgical vessels, such as copper smelters, for blowing air into the molten bath. In these situations, targeting the melt with the laser, as opposed to nearby tuyere accretions, may be assisted by imaging the end of the tuyere on a video camera installed in the probe head.

Furthermore, LIBS analysis typically requires data averaging and processing of numerous spectra. This is especially true for measurements through reacting tuyeres where turbulent bubble motion and chemical reaction at bubble surfaces result in highly variable spectral intensity and appearance. For copper smelting the thickness of the reaction layer depends on the exposure time of the molten bath to oxygen in the blown air.

In one aspect, the invention is directed to a method of analyzing a molten or liquid material by laser induced spectrography. The method comprises steps of preparing, by a flow of a gas, a portion of the material to be a representative in its composition and sending at least one laser pulse to the prepared portion to produce a plasma of the material. The method further comprises steps of transmitting radiation generated by the plasma to a spectrum analyzer and analyzing the spectrum of the radiation for the composition of the material.

In a further aspect, method comprises a further step of injecting a gas under pressure through a tube to produce a bubble inside the material, the inner surface of the bubble being the prepared portion of the material.

In a yet another aspect, the invention uses a plurality of laser pulses to produces series of measurements for real-time analysis.

In view of the above, the object of the present invention is to provide a method and apparatus which permit reliable analysis of a molten material by focusing laser pulses on the surface of that molten material. Also, the invention provides a means for direct monitoring of a molten material with a LIBS system, while overcoming interference associated with oxides or other products of surface reaction, thereby achieving efficient continuous LIBS analysis of the underlying molten material. The invention, through use of a large number of laser pulses and signal processing, may also permit the simultaneous discrimination and analysis of surface layers or contamination, and underlying bulk molten material. Furthermore, the invention may also by such means permit the simultaneous analysis of multiple phases of molten material, or molten and solid materials with or without surface layers or contamination. The above-mentioned discrimination of surface reaction layers, surface contamination or phases depends on their spatial distribution relative to the volumes ablated by successive laser pulses allowing their variable, and partially substantial, representation in the analysed plasma emissions.

In accordance with one aspect, the invention is directed to a laser induced spectrography apparatus for analyzing a molten or liquid material. The apparatus comprises a tube having a transparent window at one end and for injecting a gas under pressure into the material to prepare a portion of the material, representative of its composition, and a laser source for sending a pulsed laser beam through the tube and the window toward a prepared portion to produce a plasma of the material. The apparatus further comprises an optical arrangement for transmitting radiation from the plasma through the tube and window, and a spectrum analyzer for analyzing the radiation to determine the composition.

The present invention also uses the blowing of air, or an appropriate gas, to both perturb said surface and thus enable the laser to repeatedly sample a fresh surface on the melt, and remove aerosols and particles from the focal volume to prevent them from interfering with measurement. Furthermore, the use of blowing air or an appropriate gas by the present invention enables the removal of metallic vapor and particles splashed by the laser pulse that prevents them from absorbing the light emitted by the laser produced plasma on the molten surface. The present invention enables assisted targeting of the laser on the melt, as opposed to nearby accretions, by imaging the end of the tuyere on a video camera.

Accordingly, one object of this invention is to provide an improved method and apparatus for in-situ transient spectroscopic analysis of molten material.

A further object of this invention is to provide an apparatus that facilitates reliable real time LIBS analysis by forming bubbles in the molten material thereby enabling the laser to repeatedly sample fresh surfaces of these bubbles.

According to one aspect of the present invention an apparatus is provided for the optical analysis of the concentrations of one or more elements in a molten material by laser-induced plasma spectroscopic analysis. The apparatus comprises a means for emitting and focusing laser pulses on a surface of the molten material to generate a plasma that emits optical radiation that contains elemental radiation derived from separate compositional elements of the molten material; an appropriate blowing gas to substantially prevent drops, which are ejected from the molten material in response to the incident energy, from accumulating on an optical window of said optical system; and to remove aerosols from the focal volume of the laser beam.

According to other aspects of the present invention the apparatus comprises a substantially collinear laser beam for sampling with the optical axis of the collection system for measuring the radiation spectrum, including the specific line emissions that are representative of selected elements present in the molten material; and data processing means for determining the concentration of the selected elements by comparison with formerly established calibration curves obtained by using standard samples with different elemental concentrations independently measured by established laboratory techniques.

According to another aspect of the present invention, the detecting step includes sampling and measuring the radiation spectrum, including the specific line emissions that are representative of selected elements present in the molten material using a substantially collinear optical system and spectrometer; and processing the data to determine the concentration of the selected elements by comparing them with formerly established calibration curves obtained by recording the normalized signal levels corresponding to samples with different elemental concentrations independently measured by established laboratory techniques.

According to other aspects of the present invention the detecting step includes using a photodiode array, an intensified CCD camera, or photomultipliers individually positioned to detect both emissions from elements present in the molten material and background radiation.

BRIEF DESCRIPTION OF THE DRAWINGS

These and other objects, features and advantages of the present invention will become apparent from a consideration of the following detailed description of the invention in conjunction with the attached drawing in which.

DETAILED DESCRIPTION

In one of its embodiments, a LIBS probe of the present invention comprises a tube to gain access to the molten material by blowing appropriate gas through that tube, means for conveying radiation emitted by the thus excited plasma to a spectrometer, and means for detecting and analyzing radiation characteristic of elements present in the liquid.

Figure 1:
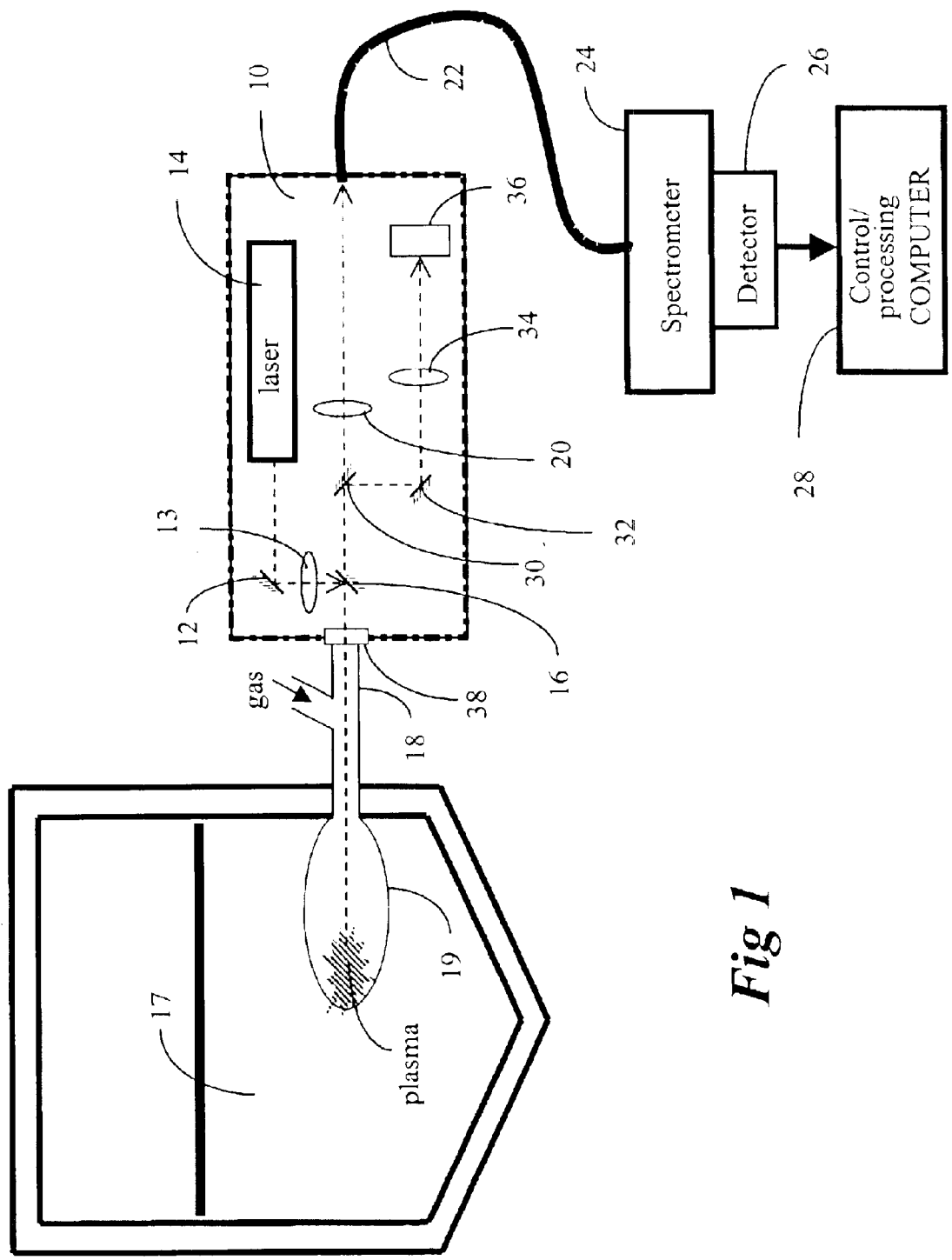
FIG. 1 shows, schematically, LIBS system for molten materials in accordance with one embodiment of the invention.

FIG. 1 is a schematic illustration of the apparatus according to one embodiment of the present invention. The individual components shown in outline or designated by blocks in these figures are all well-known in the LIBS arts, and their specific construction and operation are not critical to the operation or best mode for carrying out the present invention. The probe 10 includes a first mirror 12 that reflects a laser pulse from a laser source head 14 to a focusing lens 13. The second (dichroic) mirror 16 reflects the laser pulse to the surface of molten material 17 through a quartz window 38 and a tube 18 in which gas is blown at high pressure to produce a bubble 19 in the molten material. As shown in FIG. 1, plasma is formed at the surface of the molten material inside the bubble. Light emitted by the plasma, after passing through the quartz window 38, dichroic mirror 16, partially reflecting mirror 30, is focused by a second lens 20 at the entrance of fiber optic cable 22. The light is guided by the fiber optic to the spectrometer 24. Detection signals generated by a photodiode array or a CCD camera or PMs (photomultipliers) of a detection portion 26 of the spectrometer are supplied to the computer control-processing unit 28 for processing and treatment evaluation of data to determine the concentration of various elements within the molten material.

Figure 4:
FIG. 4 shows a typical image of the end of the tuyere by a video camera installed in the probe head.

To assist targeting the laser on the melt, as opposed to nearby accretions at the outlet of the tube 18 in the molten metal, a partially reflecting mirror 30 reflects a given proportion of the light emitted by the surface of the melt to another mirror 32 which reflects the light to a lens 34. The lens 34 focuses the light on the video camera 36. FIG. 4 shows a typical resulting image. This figure shows an image of the plasma at the bubble surface which is visible through the hole in the surrounding dark irregularly shaped accretion. Using such an image, the operator could target the melt instead of the accretions. It is also possible to perform this targeting operation automatically by mounting the probe on a robotic system and performing image analysis.

Blowing a gas through the tube at a sufficient pressure and flow prevents the debris, particles, or drops of molten material generated by the laser pulse focused on the sample from reaching the quartz window 38. Blowing also clears aerosols formed by the laser pulse from the path of the laser beam, thus avoiding aerosol absorption of subsequent laser pulses. Furthermore, blowing clears the tube from metallic vapor, thus preventing the absorption of the light emitted by the plasma. A specific gas or a mixture of gas such as air can be used for blowing and at the same time for inducing a specific reaction with molten material under process and analysis. Different components in the molten material react differently to form different layers and LIBS with pulsed laser can discriminate these layers, as they grow.

Figure 2:
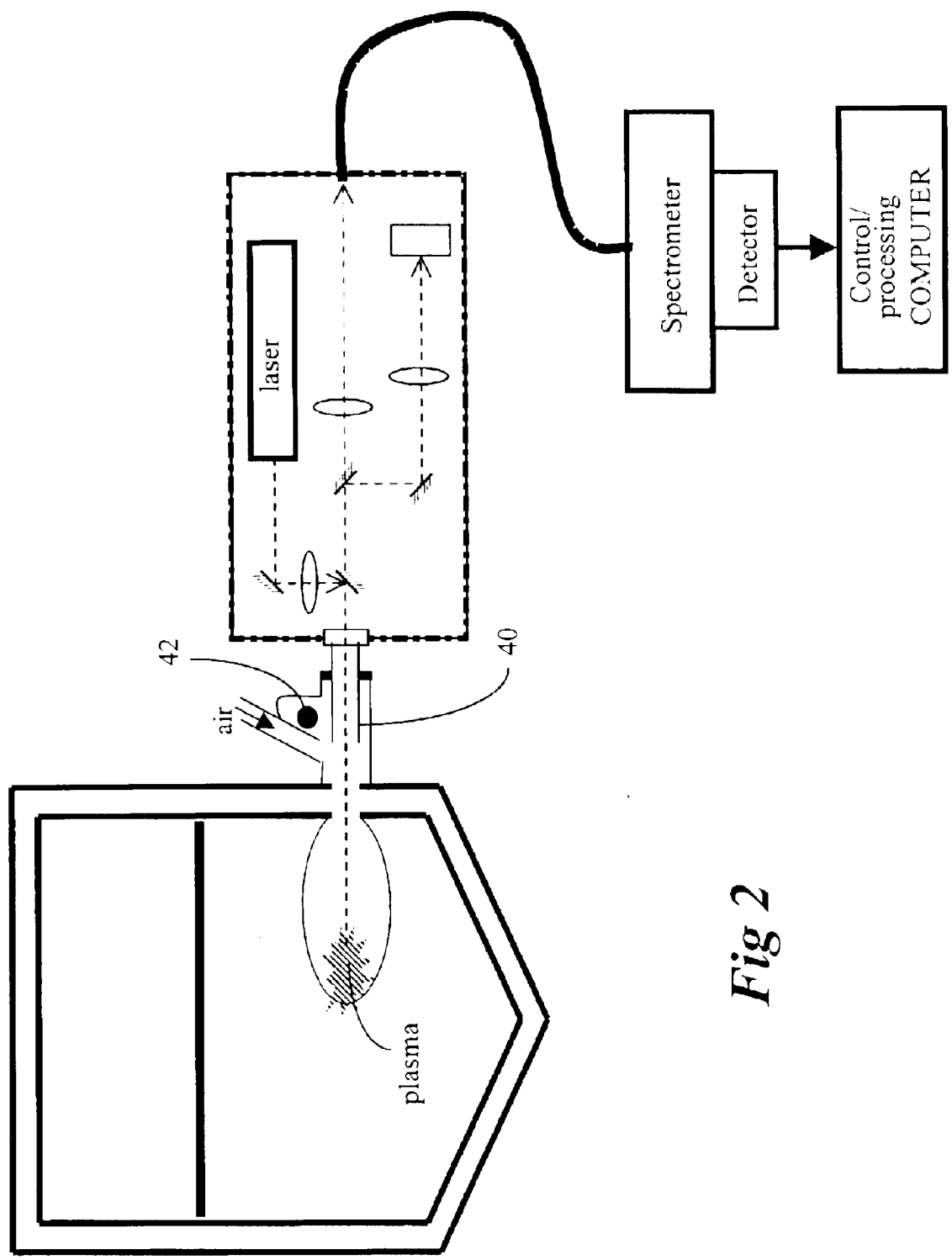
FIG. 2 is a schematic illustration of the LIBS system in accordance with another embodiment for use in composition monitoring of the molten matte through a tuyere used in the copper smelting.
Figure 3:
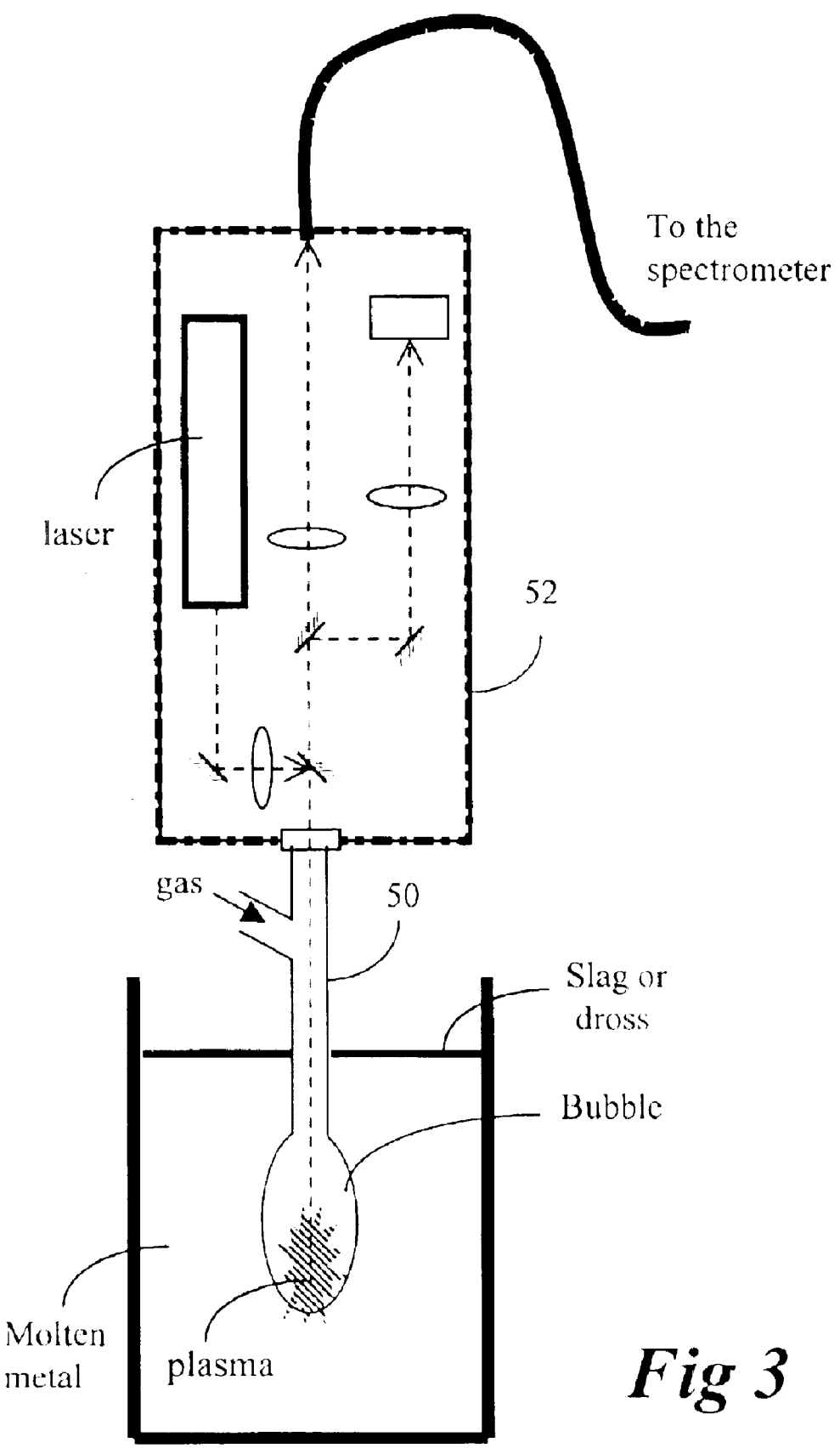
FIG. 3 shows yet another configuration showing a schematic of the LIBS probe for monitoring the molten metal.

This invention was found useful for composition monitoring of the molten matte and blister copper inside copper smelting vessels such as the Noranda Reactor and Pierce Smith converters. Matte is being primarily composed of iron and copper sulphides, while blister copper, produced at a late stage in the smelting process, exceeds 99% copper. Copper converters are equipped with several tuyeres through which air at high pressure is injected to oxidize the sulphur and effect other metallurgical transformations required for the eventual production of anode copper. In this case a variant of the embodiment of FIG. 1 is used and is shown in FIG. 2. As shown in FIG. 2, the LIBS probe is fitted with a short steel tube 40 of about 1.25" inner diameter to penetrate and displace the tuyere silencer's ball seal 42. The tube is short enough not to obstruct the air flow through the tuyere. The melt temperature is typically 1200 deg. C., and an oxygen enriched air flow is 700 scfm (standard cubic feet per minute). In other applications, such as the analysis of molten zinc alloys, a smaller tube, or tuyere, may be specifically introduced for the LIBS measurement, and gas flow of about 1litre per minute may be sufficient. In this case, an embodiment similar to that of FIG. 1 is used to monitor the molten zinc and is shown in FIG. 3. In this figure, a tube 50 of the probe 52 is introduced into the molten metal at vertical position allowing the laser to sample fresh metal inside the bubble free from the slag. The tube of the probe can be also introduced into the molten metal at certain angle from the vertical and/or the end of the tube can be shaped to improve the control of the bubbles.

A suitable choice of laser with sufficient power to excite plasma through copper smelting tuyeres to emit radiation characteristic of the composition of the molten material is the Big Sky Model CFR 400 Nd:YAG 400 mJ NIR laser, in combination with a 200 cm focal length focusing lens.

Referring back to FIG. 1, optical emission from the plasma passes through a protective window 38 that is substantially collinear with the laser beam. The emission is separated from the path of the laser beam by a dichroic mirror 16 and focused by a lens 20 into optical fibers 22, whereby it is conveyed for analysis to an optical spectrometer 24. A 0.35 m Czerny-Turner spectrometer with a 50 micron slit width and a 3600 groove/mm grating may be used in conjunction with a gated intensified CCD camera 26, manufactured by Andor Technology. Alternatively, a photodiode array detector, or photomultipliers individually positioned, with or without ancillary optics such as mirrors of fibers, to detect both emissions from elements present in the molten material and background radiation, may provide useful measurements. Selection of spectral peaks to be measured depends on the application. For the analysis of iron in molten matte to be discussed below, the atomic emission peak at 404.5 nm yields a linear calibration from 100 ppm to at least 5%, using an acquisition delay of 2 microseconds and integration time of 10 microseconds.

According to another aspect of the present invention, a method for optically analyzing the concentrations of one or more elements in a molten material by laser-induced plasma spectroscopic analysis, comprises steps of emitting and focusing successive laser pulses on the surface of a molten material to generate optical plasma emissions containing radiation derived from the separate compositional elements of the molten material; whereby the minor reacting element ratioed to the major element for a set of measurements is sorted in ascending order. Where the concentration of the minor reacting element in the reaction product layer exceeds that in the underlying smelter bath, the lowest ratio obtained by linear extrapolation to the origin of the x-axis of the sort is taken as representing the concentration of the minor element in the bath. Higher values of this ratio primarily result from variable amounts of the element in reaction product on bubble surfaces being included in the measurement. Conversely, for elements that are substantially absent from the reaction product layer, extrapolation of the element ratios to the lowest sort order essentially removes the masking or diluting effect the layer has on the analysis.

Figure 5:
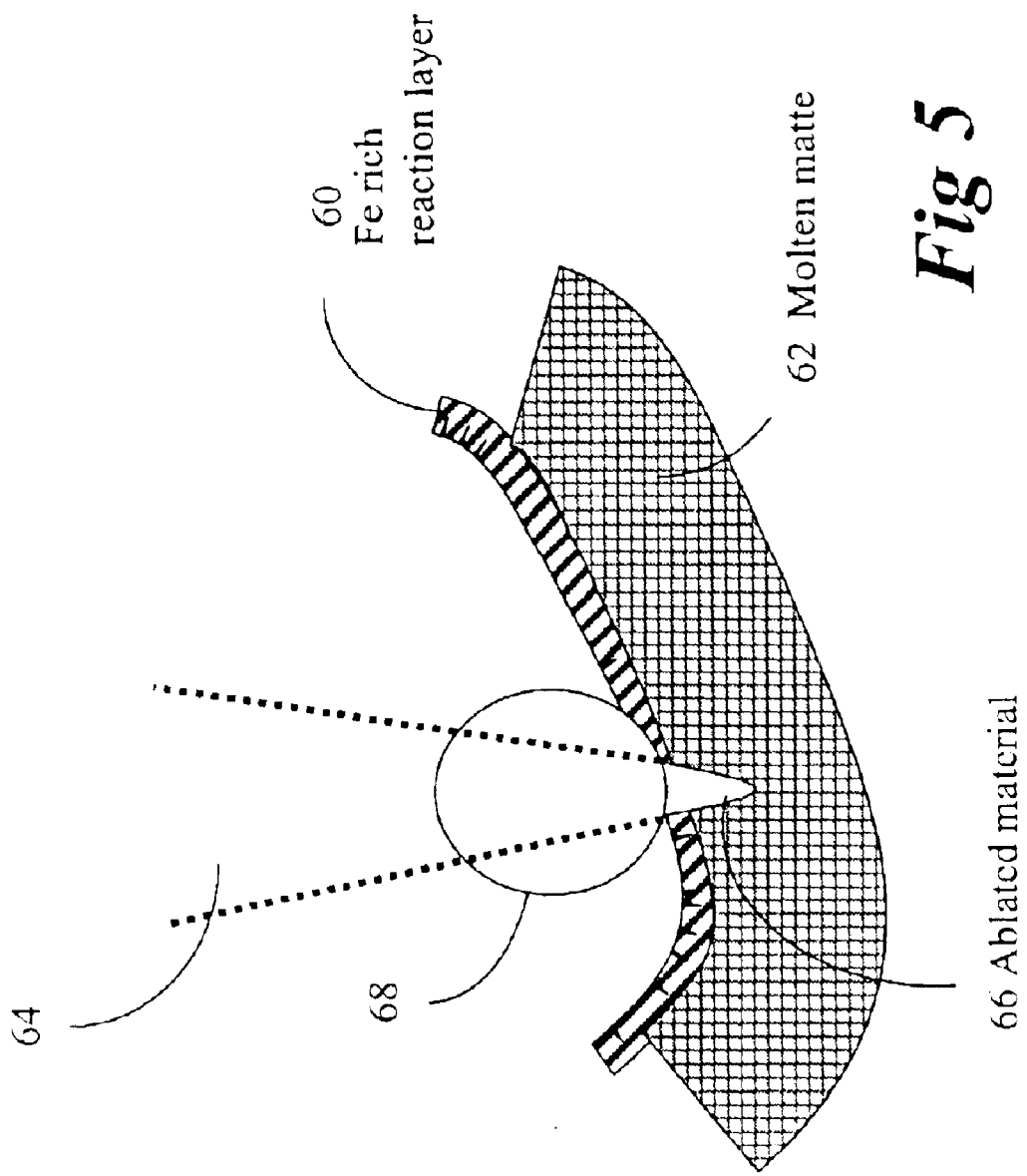
FIG. 5 is a drawing which shows a typical ablated volume from the molten material by the laser in the focal volume which includes the iron rich reaction layer present during the smelting of copper matte.
Figure 6:
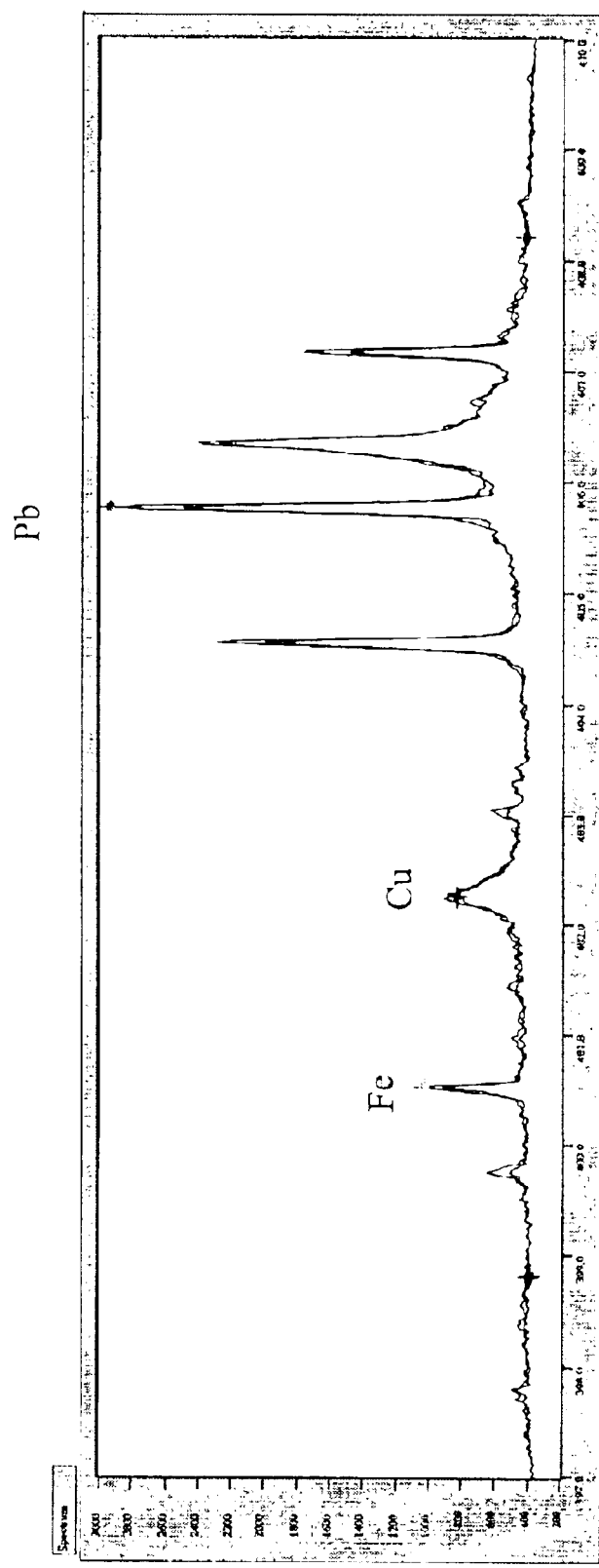
FIG. 6 compares typical spectra from molten matte from the lowest region of the Fe/Cu sort plot, and for solid accretions (solid matte) during copper smelting.

Returning to the application of composition monitoring of the matte in copper smelting, FIG. 5 shows an iron rich oxide reaction layer 60 on the inner surface of a molten matte bubble 62 blown with oxygen enriched air. The figure also shows a laser beam 64, material 66 ablated by the laser and plasma 68. Layer 60 results from the preferential oxidation of the iron sulphide in the molten bath. The oxidation of copper sulphide takes place preferentially after the oxidation of iron sulphide has finished in the smelting pyrometallurgical process. In the Noranda Process Reactor, continuous analysis of iron is especially important to maintain a concentration that inhibits the oxidation of copper which leads to excessive refractory corrosion. The thickness of the reaction layer 60 depends on the exposure time of the surface to the surrounding gas. For a fresh surface when the thickness of the oxide layer is thin compared to the ablation depth of the laser, the plasma is substantially derived from the molten bath. In this case the observed spectrum is very similar to the one obtained from solid material (such as the deposited accretions at the tip of the tuyere) and is representative of the bulk. Such a case is shown in FIG. 6. The spectrum was obtained from an approximately 1 mm-diameter spot at the surface of matte containing 3% of iron by firing a single laser pulse shot of 280 mJ energy provided by a YAG laser at a wavelength of 1064 nm. When the thickness of the oxide layer, on the other hand, becomes significant compared to the ablation depth of the laser, the plasma is derived from a combination of the reaction layer and the molten bath. For thick oxide layers compared to the laser's ablation depth, the laser is prevented from reaching the bulk of the molten material, and the resulting spectra thus provide information on the reaction layer and not the bath.

Figure 7:
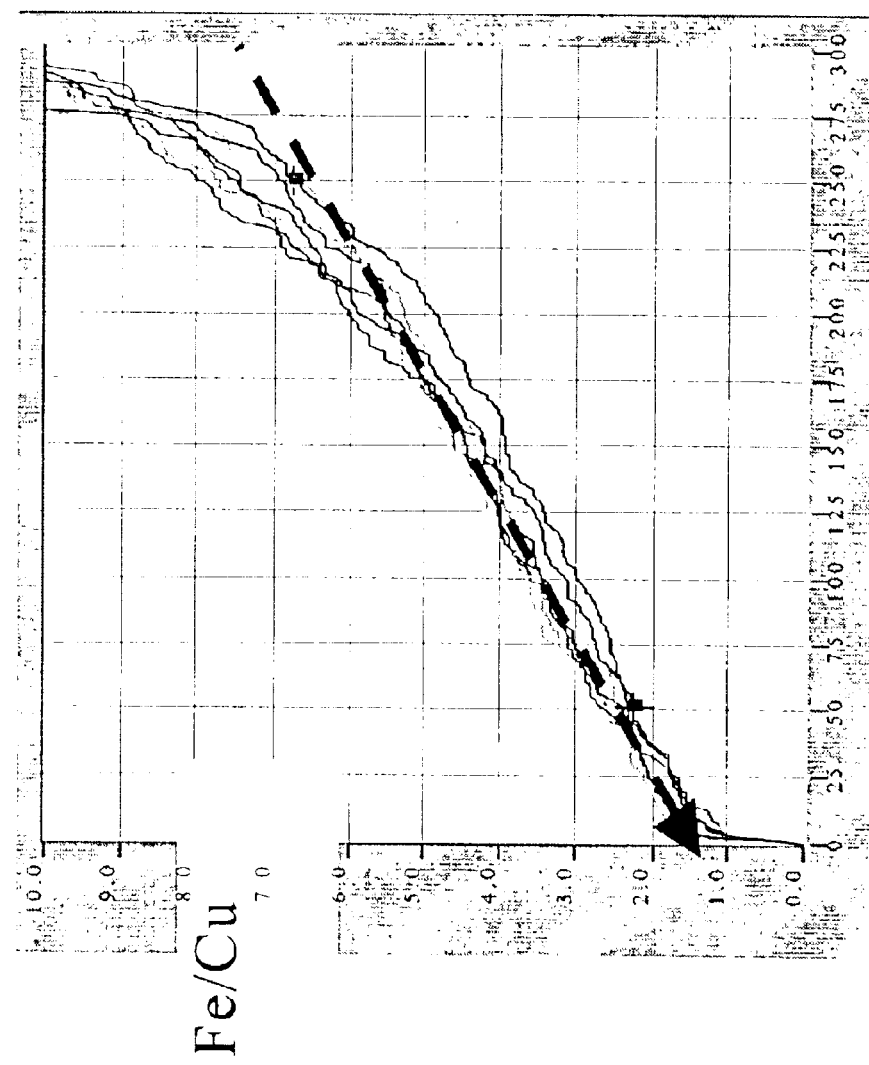
FIG. 7 shows a sorting of Fe line/Cu line ratio.

Since the surface of the bubble is rapidly oxidized and the condition of thin iron-rich reaction layer is encountered infrequently, a method had to be devised to estimate correctly the bulk iron concentration. The estimate can be done by a method based on sort plots such as those shown in FIG. 7. The abscissa and ordinate of the six plots in this figure correspond, respectively, to the rank and magnitude of the ratios of the iron 400.5 nm to copper 402.2 nm peak intensities for six 300 spectra data files sorted in ascending order of intensity ratio. In other words, one series of 300 consecutive laser shots produced 300 peak ratio measurements. These ratio measurements were ranked in ascending order. Six series of these shots were conducted and measurements are plotted in FIG. 7. The material targeted was molten copper matte. It is understood that the higher iron to copper line ratio values correspond to thick iron rich reaction layers compared to laser ablation depths. FIG. 7 indicates that higher ratio values in the sort plots do not contribute to the measurement of iron in the bulk of the bath, and should therefore be eliminated. As seen by an arrow in the figure, extrapolation of the linear part of the copper-iron ratio sort plot to obtain the Y-axis intercept at the X-axis origin provide a value representative of the iron concentration in the melt.

Figure 8:
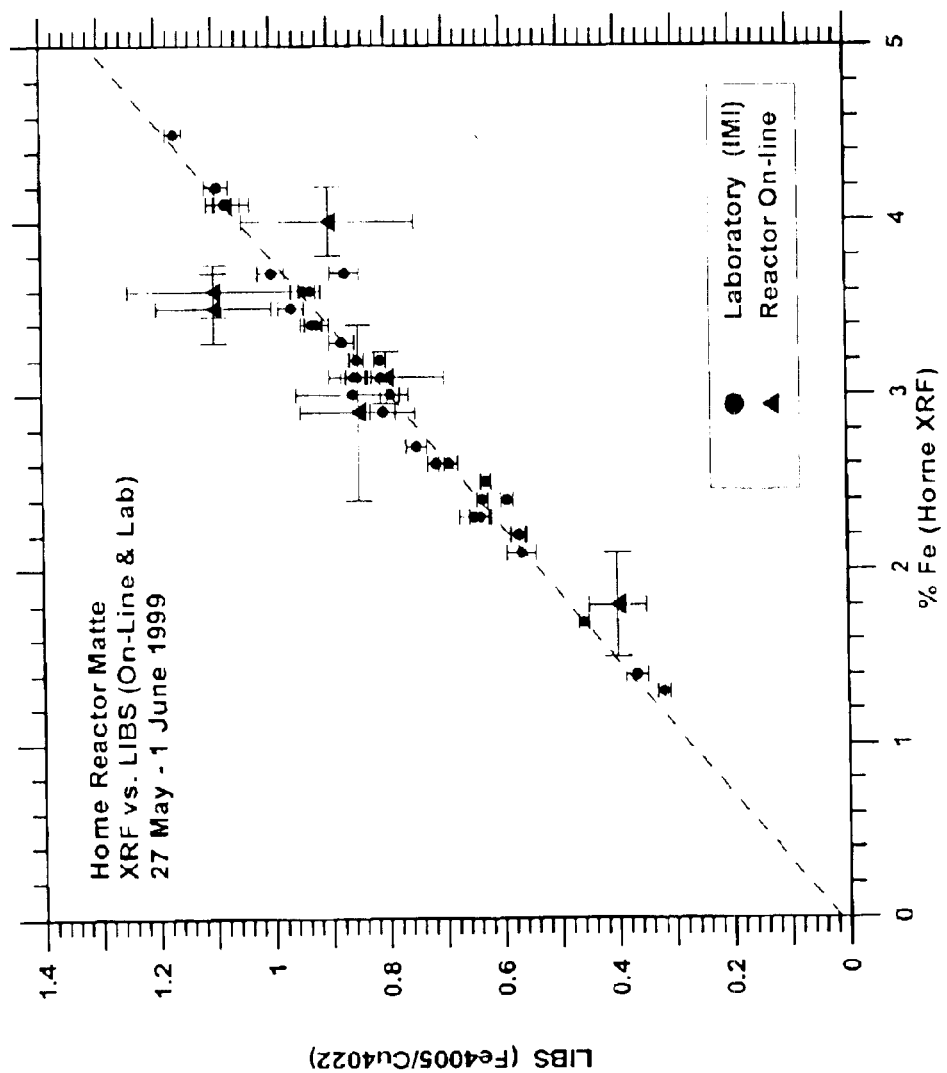
FIG. 8 shows a comparison between the LIBS and conventional techniques for iron in matte.
Figure 9:
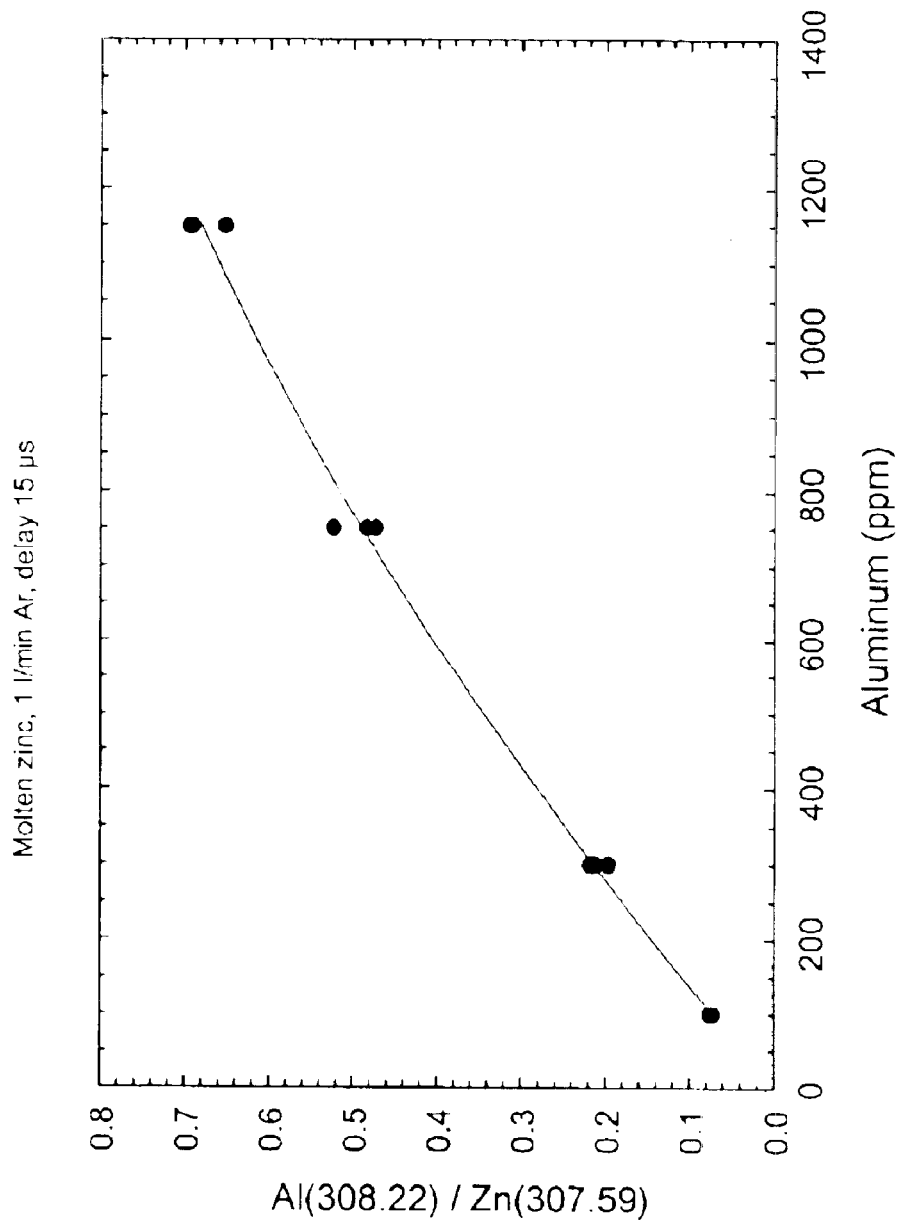
FIG. 9 shows a calibration curve for aluminum in molten zinc.

FIGS. 8 and 9 show respectively calibration curves for iron in matte and aluminum in molten zinc. FIG. 8 shows a calibration curve for the iron measurement obtained by focusing laser pulses on the surface of molten matte. For quantitative analysis by laser-induced plasma spectroscopy, elements are monitored by the measurement of spectral line intensities, which, for properly selected lines, are proportional to the species concentrations. These line intensities are affected by several parameters. In particular, they are highly dependant on the amounts of vaporization and the degree of ionization, which can change as a function of laser wavelength, laser fluence, pulse-to-pulse variability, sample surface morphology, ambient gas pressure, and ambient gas species. When creating bubbles inside the molten material by blowing an appropriate gas through the tuyere (oxygen enriched air in the case of molten matte), the variation of the shape and location of these bubbles changes the angle of incidence of the laser beam at the molten material surface, which, in turn, can change the fluence of the laser, and the line intensity. Consequently meaningful information is obtained by plotting the ratio of 2 lines, e.g. in the case of copper smelting the ratio of an iron line to that of a copper one (as shown in FIG. 8).

This invention may be applied in a number of industrial processes, such as the processing, alloying and use of molten metals. For example, measurements may be made during pyrorefining of blister copper to monitor the removal of minor elements such as bismuth and lead. Preparation of aluminum, magnesium and zinc alloys may be better controlled through the continuous in-situ analysis of alloying additions. The compositions of non-metallic liquids at elevated temperatures, such as fused salt electrolytes employed in the production of aluminum and magnesium, may also be monitored. Industrial processes, such as zinc galvanizing, where the concentrations of aluminum and iron additions change as a result of differential uptake and dross formation, may also be better controlled through continuous on-line analysis.

FIG. 9 shows a calibration curve obtained for aluminum additions in a zinc bath to control the process of galvanization. Here again measurement accuracy is improved by the setup of this invention. Al and Zn spectral lines are measured and the curve is plotted in the intensity ratio of Al/Zn along Y axis against Al concentration along the X axis. Moreover this arrangement lends itself to the analysis, and thereby continuous composition control, of zinc baths through simple access to the molten metal by means of an alumina or other suitable tube.

Moreover, application of this invention is not limited to high temperature liquids, since aqueous and other solutions, used, for example, in the refining and electrowinning of copper, may also be analyzed. This invention is also applicable to the monitoring of various chemical or electrochemical processes performed in the liquid phase. The gas blown into the liquid to create bubbles can be either used for producing the reaction or could be an inert gas.

The embodiment described above uses a single laser pulse. It is known as it has been described in U.S. Pat. No. 6,008,897 Dec. 28, 1999 Sabsabi et al that the use of a second laser pulse could increase significantly sensitivity. A second laser pulse originating from the same laser unit or an independent laser whose beam is sent collinearly to the first beam by using suitable mixing optics could then be advantageously used in some cases with a moderate increase of complexity.

It has also be found by Detalle et al as described in U.S. patent application Ser. No. 10/046,227 filed on Jan. 16, 2001 for "Method and Apparatus for Enhanced Laser Induced Plasma Spectroscopy using Mixed-Wavelength Laser Pulses" and by St-Onge et al (Spectrochimica Acta B, Vol. 57, pp.121–135, 2002) that sending at the same time several pulses at different wavelengths (e.g. infrared and ultraviolet) increases sensitivity and this approach can also be used with the described system for analysis of molten or liquid materials.

What has been described is an improved method and apparatus for in-situ transient spectroscopic analysis of molten materials. While the present invention has been described with respect to what is presently considered to be the preferred embodiment, it is to be understood that the invention is not limited to the disclosed embodiment. To the contrary, the invention is intended to cover various modifications and equivalent arrangements included within the spirit and scope of the appended claims. Therefore, the scope of the following claims is to be accorded the broadest interpretation so as to encompass all such modifications and equivalents.

What is claimed is:

1. A method of analyzing a molten or liquid material by laser induced spectrography, comprising steps at preparing a prepared portion of the material representative of its composition by a flow of a gas injected under pressure through a tube to produce a bubble inside the material, the inner surface of the bubble being the prepared portion of the material;

sending at least one laser pulse through the tube to the prepared portion to produce a plasma of the material;

transmitting radiation generated by the plasma through the tube to a spectrum analyzer, and analyzing a spectrum of the transmitted radiation to determine a composition of the material.

2. The method according to claim 1, wherein the gas is selected from a group of gases which include air, an inert gas and any of reactive gases used for processing of the material.

3. The method according to claim 2, wherein the gas is a reactive gas selected from a group of gases which are used for processing of the material, and the method further comprising step of:

controlling processing of the material in response to the composition so determined.

4. The method according to claim 3, further comprising a step of:

optically monitoring through the tube the prepared portion to assist targeting the laser pulse.

5. The method according to claim 4, wherein the step of analyzing comprises a step of:

plotting a ratio of two spectral lines, one of said spectral lines related to a specific constituent in the material and the other of said spectral lines related to a constant major constituent.

6. The method according to claim 5, wherein the step of analyzing further comprises a step of:

finding by extrapolation a ratio representative of a bulk of the material.

7. The method according to claim 6, wherein the step of analyzing further comprises a step of:

calibrating the composition thus far determined by using a calibration curve established on samples which have been calibrated through independent laboratory measurements.

8. The method according to claim 7, wherein the processing of the material is copper smelting and the specific constituent is iron and the constant major constituent is copper.

9. The method according to claim 8, further comprising a step of:

adjusting an angle of insertion of the tube into the material to control formation of the bubble.

10. The method according to claim 7, wherein the processing of the material is a hot dip galvanization process.

11. The method according to claim 10, further comprising a step of:

adjusting an angle of insertion of the tube into the material to control formation of the bubble.

12. The method according to claim 4, further comprising steps of:

sending a series of laser pulses to produce a plurality of plasmas, and repeating the step of analyzing for each of the plurality of plasmas to determine the composition of the material.

13. The method according to claim 12, wherein the step of analyzing comprises a step of:

plotting a ratio of two spectral ones, one of said spectral lines related to a specific constituent in the material and the other of said spectral lines related to a constant major constituent.

14. The method according to claim 13, wherein the step of processing comprises a step of:

finding by extrapolation a ratio representative of a bulk of the material.

15. The method according to claim 14, wherein the step of analyzing further comprises a step of:

calibrating the composition thus far determined by using a calibration curve established on samples which have been calibrated through independent laboratory measurements.

16. The method according to claim 15, wherein the processing of the material is copper smelting and the specific constituent is iron and the constant major constituent is copper.

17. The method according to claim 16, further comprising a step of;

adjusting an angle of insertion of the tube into the material to control formation of the bubble.

18. The method according to claim 15, wherein the processing of the material is a hot dip galvanization process.

19. The method according to claim 18, further comprising a step of:

adjusting an angle of insertion of the tube into the material to control formation of me bubble.

20. The method according to claim 4, further comprising steps of:

sending a series of laser pulses of different wavelengths to produce a series of plasmas, and repeating the step of analyzing a spectrum of each plasma to determine the composition of the material.

21. The method according to claim 20, wherein the step of analyzing comprises a step of:

plotting a ratio of two spectral lines, one of said spectral lines related to a specific constituent in the material and the other of said spectral lines related to a constant major constituent.

22. The method according to claim 21, wherein the step of processing comprises a step of:

finding by extrapolation a ratio representative of a bulk of the material.

23. The method according to claim 22, wherein the step of analyzing further comprises a step of:

calibrating the composition thus far determined by using a calibration curve established on samples which have been calibrated through independent laboratory measurements.

24. The method according to claim 23, wherein the processing of the material is a hot dip galvanization process.

25. The method according to claim 23, wherein the processing of the material is copper smelting and the specific constituent is iron and the constant major constituent is copper.

26. The method according to claim 25, further comprising a step of:

adjusting an angle of insertion of the tube into the material to control formation of the bubble.

27. The method according to claim 24, further comprising a step of:

adjusting an angle of insertion of the tube into the material to control formation of the bubble.

28. A laser induced spectrography apparatus for analyzing a molten or liquid material, comprising:

a tube for injecting a gas under pressure into the material to prepare a portion of the material representative of its composition, said tube having a transparent window at one end;

a laser source for sending a pulsed laser beam through tho tube and the window toward the prepared portion to produce a plasma of the material;

an optical arrangement for transmitting radiation from the plasma through the tube and window, and a spectrum analyzer for analyzing the radiation to determine a composition of the material.

29. The apparatus according to claim 28, wherein at least a portion of the tube is made of a resistance material and is adapted to be immersed in the material.

30. The apparatus according to claim 29, wherein the optical arrangement comprises a combination of lenses, mirrors and fiber optics.

31. The apparatus according to claim 30, further comprising:

a vision system for monitoring the prepared portion to assist in targeting the pulsed laser beam.

32. The apparatus according to claim 31, further comprising:

a gas injecting mechanism for injecting the gas to create a bubble inside the material when the tube is immersed therein.

33. The apparatus according to claim 31, wherein the gas injected by the gas injecting mechanism prevents accumulation of aerosols and ablation debris along the laser beam path.

34. The apparatus according to claim 32, wherein a tip of the tube is designed to control formation of the bubble.

35. The apparatus according to claim 28, wherein the tube is designed or insertion into a tuyere provided on a processing equipment of the material, and such that it does not disturb the flow of the gas through the tuyere.

36. The apparatus according to claim 35, wherein the optical arrangement comprises a combination of lenses, mirrors and fiber optics.

37. The apparatus according to claim 36, further comprising:

a vision system for monitoring the prepared portion to assist in targeting the pulsed laser beam.

38. The apparatus according to claim 37, further comprising a gas injecting mechanism for injecting the gas to create trio bubble inside the material when the tube is immersed therein.

39. The apparatus according to claim 37, wherein the gas injected by the gas injecting mechanism prevents accumulation of aerosols and ablation debris along the laser beam path.

* * * * *